United States Patent
Glick et al.

(10) Patent No.: US 9,642,690 B2
(45) Date of Patent: May 9, 2017

(54) SUTURE LOADED UMBILICAL MESH

(75) Inventors: Jonathan Glick, Hamden, CT (US); Rich Schiretz, Burlington, NC (US)

(73) Assignee: Covidien LP, Mansfield, MA (US)

(*) Notice: Subject to any disclaimer, the term of this patent is extended or adjusted under 35 U.S.C. 154(b) by 67 days.

(21) Appl. No.: 14/003,575

(22) PCT Filed: Mar. 22, 2012

(86) PCT No.: PCT/US2012/030101
§ 371 (c)(1),
(2), (4) Date: Sep. 6, 2013

(87) PCT Pub. No.: WO2012/129391
PCT Pub. Date: Sep. 27, 2012

(65) Prior Publication Data
US 2014/0025094 A1   Jan. 23, 2014

Related U.S. Application Data

(60) Provisional application No. 61/467,158, filed on Mar. 24, 2011.

(51) Int. Cl.
*A61B 17/08* (2006.01)
*A61F 2/00* (2006.01)

(52) U.S. Cl.
CPC .... *A61F 2/0063* (2013.01); *A61F 2250/0097* (2013.01)

(58) Field of Classification Search
CPC ............ A61F 2/0063; A61F 2002/0068; A61F 2002/0072; A61F 2/0045; A61F 2/02; A61F 2/0036; A61F 2002/30617; A61F 2002/302; A61F 2002/30235; A61F 2002/30909; A61F 2250/0097; A61F 2250/0051; A61F 2210/0004; A61F 13/00; A61F 15/008; A61F 2013/00157; A61F 2013/00165; A61F 2013/00182; A61F 2013/00463;
(Continued)

(56) References Cited

U.S. PATENT DOCUMENTS 4,839,215 A    6/1989 Starling et al.
7,101,381 B2 * 9/2006 Ford et al. .................... 606/151
(Continued)

FOREIGN PATENT DOCUMENTS

WO    WO 02/091953 A1    11/2002

OTHER PUBLICATIONS

International Search Report for PCT/US12/30101date of completion is Jun. 26, 2012 (one page).
(Continued)

*Primary Examiner* — Katherine M Shi
*Assistant Examiner* — Mohamed Gabr

(57) ABSTRACT

A surgical mesh includes a body portion configured to extend across a tissue defect and a plurality of fibers secured to the body portion. The plurality of fibers extends outwardly from the body portion and is gathered at a hub for handling by a clinician. In embodiments, the plurality of fibers may be coupled to the mesh via one of knitting, weaving, or interlacing each fiber through yarns forming the body portion. In other embodiments, the plurality of fibers is coupled to the mesh via one of knotting, tying, welding, adhering, and fusing each fiber to yarns forming the body portion.

14 Claims, 2 Drawing Sheets

(58) Field of Classification Search
CPC ..... A61F 2013/00834; A61B 17/00234; A61B 17/0057; A61B 17/0293; A61B 17/3423; A61B 2017/00659; A61B 2017/3419
USPC ......... 128/898; 606/99, 151, 148; 623/23.75
See application file for complete search history.

(56) References Cited

U.S. PATENT DOCUMENTS

| | | |
|---|---|---|
| 7,901,346 B2 | 3/2011 | Kovac et al. |
| 2004/0087980 A1* | 5/2004 | Ford et al. .................... 606/151 |
| 2008/0147200 A1* | 6/2008 | Rousseau et al. ......... 623/23.75 |
| 2009/0171142 A1 | 7/2009 | Chu |
| 2009/0216075 A1* | 8/2009 | Bell et al. ....................... 600/37 |
| 2009/0281558 A1 | 11/2009 | Li |
| 2011/0082478 A1 | 4/2011 | Glick et al. |

OTHER PUBLICATIONS

Supplementary European Search Report for EP 12760754.7-1662 date of completion is Oct. 27, 2014 (6 pages).

\* cited by examiner

SUTURE LOADED UMBILICAL MESH

CROSS-REFERENCE TO RELATED APPLICATIONS

This application is a National Stage Application of PCT/US12/30101 under 35USC §371 (a), which claims priority of U.S. Provisional Patent Application Ser. No. 61/467,158 filed Mar. 24, 2011, the disclosures of each of the above-identified applications are hereby incorporated by reference in their entirety.

BACKGROUND

Technical Field

The present disclosure relates to surgical meshes and, more particularly, to surgical meshes including positioning sutures for use in hernia repair.

Background of Related Art

Wound closure devices, such as sutures, filaments, and staples, as well as other repair devices, such as mesh or patch reinforcements, are frequently used to repair tissue defects, e.g., herniated tissue, and other damaged and/or diseased tissue. For example, in the case of hernias, a surgical mesh or patch is commonly used to reinforce the abdominal wall. The surgical mesh is generally sized to extend across the defect and is adapted to flex or bend in order to conform to the abdominal wall. The surgical mesh is typically held in place by adhering, suturing, or stapling the mesh to the surrounding tissue.

However, difficulties may arise during the course of a hernia repair procedure, particularly with regard to properly positioning the surgical mesh and/or securely affixing the mesh to surrounding tissue. These difficulties are often attributed to anatomical spatial constrains and/or reduced, or limited, access to the surgical site. Improper positioning or affixing of the mesh may result in re-herniation, dislodging, or repositioning of the surgical mesh relative to tissue and/or viscera entering the defect.

U.S. Pat. No. 7,828,854 discloses an implantable prosthesis for repairing or reinforcing a tissue or muscle wall defect. The prosthesis includes a first composite structure including a central portion sized and shaped to cover at least a portion of the tissue or muscle wall defect, a second composite structure having a reinforced central region, a reinforcing element positioned between the first and second structures, and at least one pulling element coupled to the reinforced central region of the second structure. The second structure is coupled to the first structure substantially only at their respective peripheries.

It would be advantageous to provide a surgical mesh with positioning elements so that the force exerted on portions of the mesh may be customized so that the mesh may be positioned against tissue in a uniform manner, regardless of surface topography.

SUMMARY

A surgical mesh includes a body portion configured to extend across a tissue defect and a plurality of fibers secured to the body portion. The plurality of fibers extends outwardly from the body portion and is gathered at a hub for handling by a clinician. In embodiments, the plurality of fibers may be coupled to the mesh via one of knitting, weaving, or interlacing each fiber through yarns forming the body portion. In other embodiments, the plurality of fibers is coupled to the mesh via one of knotting, tying, welding, adhering, and fusing each fiber to yarns forming the body portion.

The body portion of the surgical mesh includes pre-defined regions each containing a portion of the plurality of fibers. The pre-defined regions may be symmetrically arranged about the body portion. In embodiments, the portion of fibers in each pre-defined region is formed into a yarn. In embodiments, each yarn is color coded for visually identifying the pre-defined region of the body portion. In some embodiments, the yarns are commingled to form a main yarn. The yarns may be commingled via one of weaving, knitting, braiding, interlacing, twisting, fusing, and aligning.

The surgical mesh may be provided in a variety of shapes and sizes. In embodiments, the body portion of the surgical mesh is circular. In such embodiments, the pre-defined regions of the body portion may correspond to the four quadrants of the circular body portion.

In embodiments, the outer diameter of the body portion of the surgical mesh may include a stiffening ring. In some embodiments, a central portion of the body portion of the surgical mesh may include a guide through which the plurality of fibers may extend outwardly.

Methods of using the surgical mesh to repair tissue defects are also disclosed. In accordance with the present methods, a mesh is provided. The mesh includes a plurality of fibers secured to a body portion of the mesh, the plurality of fibers extending outwardly from the body portion and gathering at a hub. The mesh is inserted through a tissue defect such that the mesh extends across the tissue defect and the plurality of fibers extend proximally through the tissue defect. The tension on the plurality of fibers extending through the tissue defect may be adjusted to position the mesh uniformly against tissue. The step of adjusting the tension on the plurality of fibers may further include manipulating yarns formed from select portions of the plurality of fibers or manipulating a main yarn formed from the plurality of fibers. The method may also further include the step of applying fasteners to the mesh to secure the mesh to tissue surrounding the tissue defect.

BRIEF DESCRIPTION OF THE DRAWINGS

Various embodiments of the present disclosure are described herein with reference to the drawings wherein.

DETAILED DESCRIPTION

Figure 1:
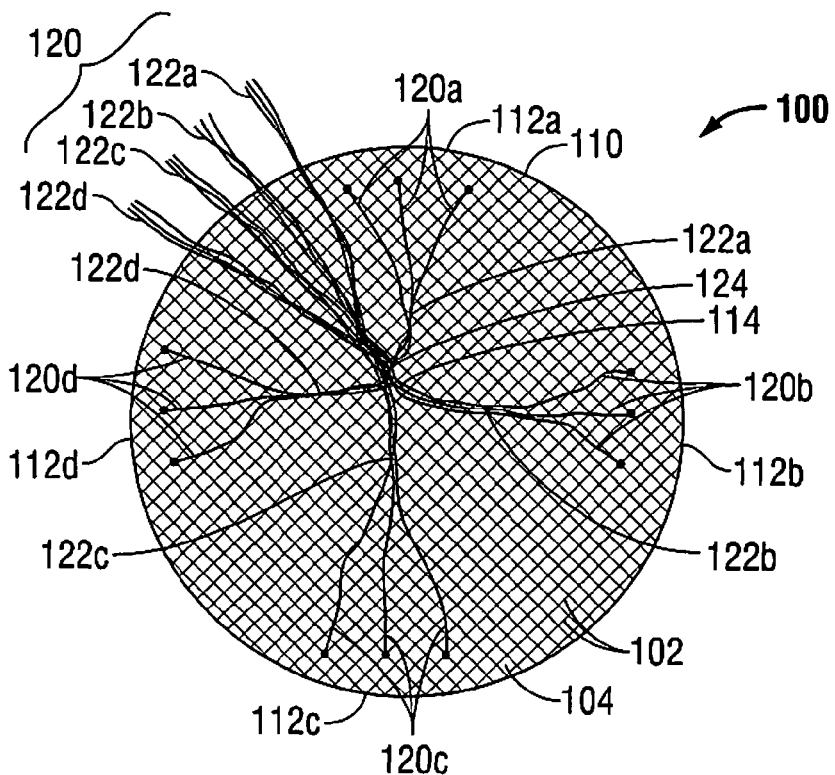
FIG. 1 is a top view of a surgical mesh in accordance with an embodiment of the present disclosure.

Surgical meshes in accordance with the present disclosure are fabricated from a textile which provides the primary structure to the implant. The surgical mesh is pre-loaded with fibers extending outwardly from the body portion for positioning and securing the implant over a tissue defect.

While the surgical meshes are especially suitable for surgical repair of hernias, it is envisioned that the meshes can be used in connection with other surgical procedures requiring repair of soft tissue defects such as muscle or wall tissue defects, pelvic organ prolapse, and urinary incontinence, for example. The meshes of the present disclosure can be in the form of sheets, patches, slings, suspenders, and other implants and composite materials such as pledgets, buttresses, wound dressings, drug delivery devices, and the like.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user. As used herein, the term "patient" should be understood as referring to a human subject or other animal, and the term "clinician" should be understood as referring to a doctor, nurse or other care provider and may include support personnel.

Referring now to FIG. 1, an embodiment of a surgical mesh 100 in accordance with the present disclosure is illustrated. Mesh 100 includes a body portion 110 formed from yarns 102 including at least two filaments which may be made of any suitable biocompatible material. Materials include biodegradable and/or non-biodegradable materials, including natural, synthetic, bioabsorbable, and non-absorbable materials, and combinations thereof. Suitable materials from which the body portion 110 may be made should have the following characteristics: sufficient tensile strength to support a fascial wall during repair of a defect in the fascial wall causing a hernia; sufficiently inert to avoid foreign body reactions when retained in the human body for long periods of time; easily sterilized to prevent the introduction of infection when the mesh is implanted in the human body; and have suitably easy handling characteristics for placement in the desired location in the body. The mesh 100 should be sufficiently pliable to conform to a fascial wall and flex with movement of the wall, while being sufficiently rigid to retain its mesh shape following transport through the tissue.

Yarns 102 may be arranged relative to each other to form openings 104 in the body portion 110 of mesh 100. Alternatively, the mesh may be formed from a continuous yarn that is arranged in loops that give rise to the openings in the mesh. In other embodiments, yarns 102 may be tightly woven so that little to no space is provided therebetween. The spacing between the yarns 102 of the mesh 100 may vary depending on the surgical application and desired implant characteristics as envisioned by those skilled in the art. For example, the openings 104 of the mesh 100 of the present disclosure may affect the mass or the tensile strength of the implant. As another example, the openings 104 may be sized to permit fibroblast through-growth and ordered collagen laydown, resulting in integration of the mesh 100 into the body.

Figure 4:
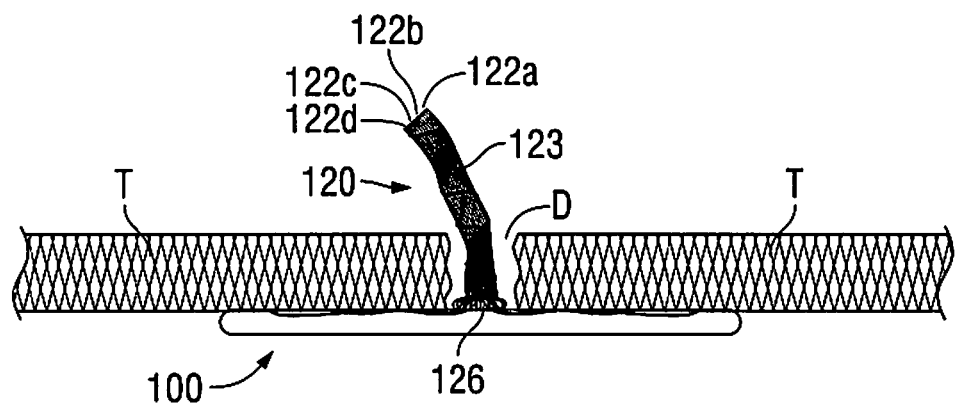
FIG. 4 is a side, cross-sectional view of a surgical mesh positioned within a tissue defect in accordance with an embodiment of the present disclosure.

Moreover, due to the variety of sizes of defects, and of the various fascia that may need repair, the mesh 100 may be of any suitable size and shape. As illustrated in the current embodiment, the mesh 100 defines a generally flat, circular configuration that is dimensioned to extend across a tissue defect "D" (FIG. 4). The yarns 102 of the body portion 110 of mesh 100 may be woven, knitted, interlaced, braided, twisted, aligned, fused, formed by non-woven techniques, or otherwise joined to form a variety of different mesh configurations and shapes. The structure of the mesh 100 will vary depending upon the assembling technique utilized to form the mesh, as well as other factors such as the type of filaments used, the tension at which the filaments and/or yarns are held, and the mechanical properties required of the mesh.

In embodiments, knitting may be utilized to form a mesh of the present disclosure. Knitting involves, in embodiments, the intermeshing of yarns to form loops or interlooping of the yarns. In some embodiments, yarns may be warp-knitted thereby creating vertical interlocking loop chains and/or may be weft-knitted thereby creating rows of interlocking loop stitches across the mesh. In other embodiments, weaving may be utilized to form a mesh of the present disclosure. Weaving may include, in embodiments, the intersection of two sets of straight yarns, warp and weft, which cross and interweave at right angles to each other, or the interlacing of two yarns at right angles to each other. In some embodiments, the yarns may be arranged to form a net mesh which has isotropic or near isotropic tensile strength and elasticity.

In embodiments, the yarns may be nonwoven and formed by mechanically, chemically, or thermally bonding the yarns into a sheet or web in a random or systematic arrangement. For example, yarns may be mechanically bound by entangling the yarns to form the mesh by means other than knitting or weaving, such as matting, pressing, stitch-bonding, needlepunching, or otherwise interlocking the yarns to form a binderless network. In other embodiments, the yarns of the mesh may be chemically bound by use of an adhesive, such as a hot melt adhesive, or thermally bound by applying a binder, such as a powder, paste, or melt, and melting the binder on the sheet or web of yarns.

The mesh may be a composite of layers. Suitable meshes, for example, include a collagen composite mesh such as PARIETEX™ (Tyco Healthcare Group LP, d/b/a Covidien, North Haven, Conn.). PARIETEX™ composite mesh is a 3-dimensional polyester weave with a resorbable collagen film bonded on one side. Examples of other meshes which may be utilized include those disclosed in U.S. Pat. Nos. 6,596,002; 6,408,656; 7,021,086; 6,971,252; 6,695,855; 6,451,032; 6,443,964; 6,478,727; 6,391,060; and U.S. Patent Application Publication No. 2007/0032805, the entire disclosures of each of which are incorporated by reference herein.

Extending from body portion 110 of mesh 100 is a plurality of fibers 120 symmetrically placed about the body portion 110. The fibers 120 may be positioned about the mesh 100 in any suitable fashion and/or location depending upon the application of use. Fibers 120 may be secured to body portion 110 in any suitable manner, such as knitting, weaving, or otherwise interlacing the fibers 120 within the yarns 102 of the body portion 110. The fibers 120 may also be secured to body portion 110 by knotting, tying, welding, adhering, fusing, etc. Alternatively, the fibers may be part of the yarns 102 making up the body portion 110 and thus, integrally formed with the body portion 110.

Body portion 110 includes pre-defined regions, e.g., four distinct regions 112a, 112b, 112c, and 112d, radially spaced about body portion 110 at the 12 o'clock, 3 o'clock, 6 o'clock, and 9 o'clock positions, respectively. As illustrated, each region 112a, 112b, 112c, and 112d is defined by each quadrant of the circular configuration of the body portion 110. Each region 112a, 112b, 112c, and 112d includes a portion 120a, 120b, 120c, and 120d of fibers 120 extending therefrom, which in turn may each be oriented, crinkled, twisted, braided, or otherwise commingled to form yarns 122a, 122b, 122c, and 122d, respectively. Yarns 122a, 122b, 122c, and 122d may be gathered at a common location or hub 124, generally about center portion 114 of body portion 110 for handling by a clinician. In embodiments, yarns 122a, 122b, 122c, and 122d may be twisted, fused, or otherwise joined at hub 124.

While each region 112a, 112b, 112c, and 112d of body portion 110 is illustrated as including three fibers 120a, 120b, 120c, and 120d, it is envisioned that any number of fibers may be disposed in each region 112a, 112b, 112c, and 112d. Thus, each region may contain the same or different number of fibers in the same or different configurations. Likewise, a mesh may include any number of regions or alternatively, the fibers may be radially spaced about the surface of the mesh and the clinician may pick and choose which fibers to utilize during use of the device. In embodiments, the un-used fibers may be cut, or in embodiments in which the fibers are fabricated from absorbable materials, the fibers may be left intact and be absorbed by the body over time.

In embodiments, the yarns 122a, 122b, 122c, and 122d, or at least the end portion thereof, may be color coded, e.g., dyed with different nontoxic colored substances, to aid the clinician in adjusting the tension on the different regions 112a, 112b, 112c, and 112d of body portion 110 by providing a distinguishing visual feature to each of the yarns 122a, 122b, 122c, and 122d. Regions 112a, 112b, 112c, and 112d of body portion 110 may also be color coded to correspond with the color coded yarns 122a, 122b, 122c, and 122d such that the clinician, for example, may observe placement of the mesh 100a through a viewing instrument and manipulate the color coded yarn corresponding to the color coded region of the mesh 100a.

Figure 2:
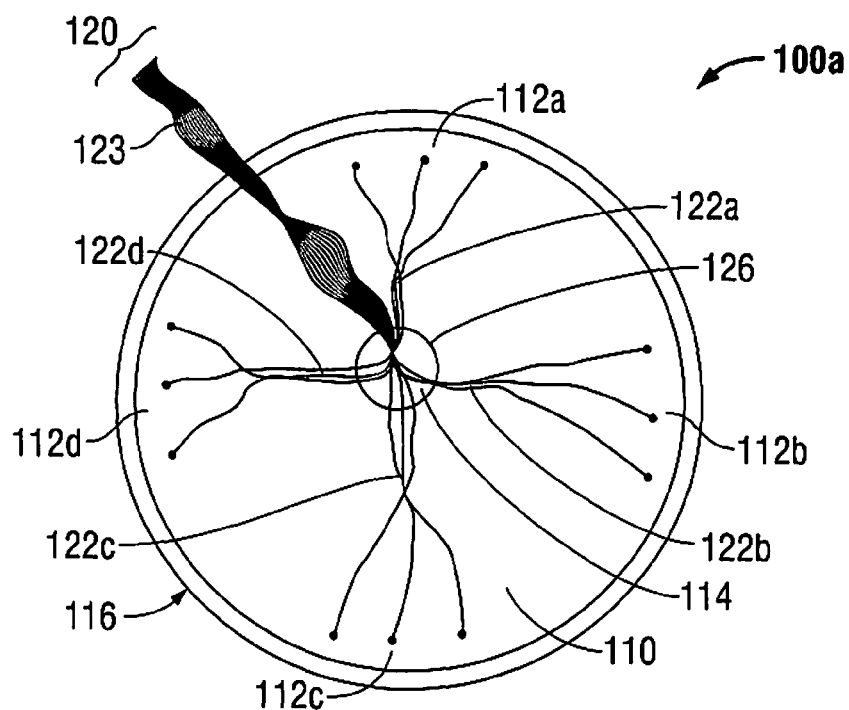
FIG. 2 is a top view of the surgical mesh of FIG. 1 including a guide and stiffening ring.

Referring now to FIG. 2, surgical mesh 100a is illustrated as including a guide 126 at center portion 114 of the body portion 110 to aid in positioning yarns 122a, 122b, 122c, and 122d. Guide 126 may be an annular structure which is adhered or otherwise engaged to center portion 114 of body portion 110, e.g., on a proximal surface of body portion 110, or may be disposed at least partially within mesh 110. Further, guide 126 may be monolithically formed, or may be formed from woven filaments of material. Yarns 122a, 122b, 122c, and 122d may be threaded or otherwise passed under or through guide 126 such that the yarns 122a, 122b, 122c, and 122d extend proximally and outwardly therethrough for grasping by a clinician.

Guide 126 may be utilized to more accurately manipulate yarns 122a, 122b, 122c, and 122d which extend therethrough due to the equally-spaced distribution of the yarns 122a, 122b, 122c, and 122d about the body portion 110, e.g., at the 12 o'clock, 3 o'clock, 6 o'clock and 9 o'clock positions in regions 112a, 112b, 112c, and 112d, respectively. Further, in this configuration, mesh 100a is also more easily secured in position due to the fact that yarns 122a, 122b, 122c, and 122d extend from central portion 114 of mesh 100a directly adjacent the tissue defect "D" (see FIG. 4), reducing the likelihood that filaments of the yarns 122a, 122b, 122c, and 122d would catch, or interfere with mesh 100a or surrounding tissue.

Moreover, yarns 122a, 122b, 122c, and 122d may be commingled to form a main yarn 123 extending from body portion 110 for ease of handling by a clinician. Main yarn 123 may be formed by weaving, knitting, braiding, interlacing, twisting, fusing, or aligning yarns 122a, 122b, 122c, and 122d. In embodiments, main yarn 123 is pre-formed, thus eliminating the need for the clinician to locate and retrieve each of the yarns 122a, 122b, 122c, and 122d from within the surgical site. In other embodiments, main yarn 123 may be formed after proper tensioning of yarns 122a, 122b, 122c, and 122d by the clinician as described in further detail below.

Further, body portion 110 may include a stiffening ring 116 to aid in preventing bunching of the mesh 100a, as well as to provide structural support and rigidity to the mesh 100a while still allowing the mesh 100a to be manipulated during insertion and positioning of mesh 100a within a tissue defect "D" (FIG. 4). Stiffening ring 116, for example, defines an annular configuration and is disposed at or near the outer periphery or diameter of body portion 110. Stiffening ring 116 may be formed from any suitable material, e.g., an absorbable or non-absorbable polymer. More specifically, the stiffening ring 116 may be formed from a resiliently deformable material to facilitate insertion of mesh 100a within a tissue defect "D" (FIG. 4) in a rolled up or folded configuration and re-opening of the mesh 100 upon placement within tissue "T" (FIG. 4). Stiffening ring 116 may also permit mesh 100 to conform to the contours of tissue surrounding the tissue defect "D" (FIG. 4). Stiffening ring 116 may be a layer of material joined to body portion 110 of mesh 100, or may comprise additional filaments within the body portion 110. As illustrated, the stiffening ring 116 is disposed outwardly of fibers 120, however, in other embodiments, at least a portion of the fibers of the mesh may extend from the stiffening ring 116.

Figure 3:
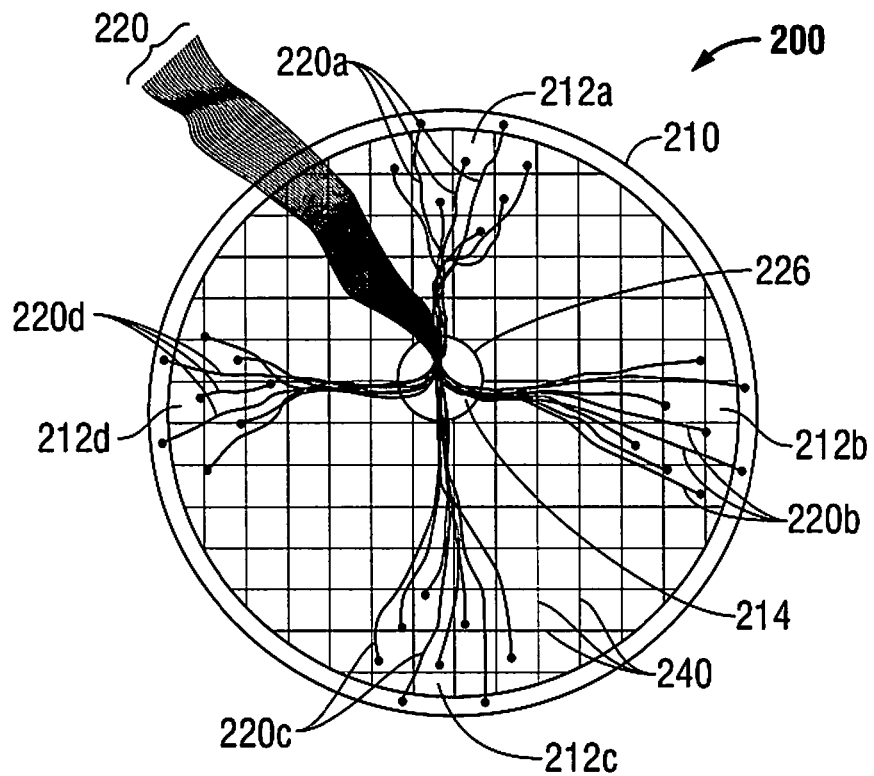
FIG. 3 is a top view of a surgical mesh in accordance with another embodiment of the present disclosure.

Turning now to FIG. 3, there is illustrated a surgical mesh 200 in accordance with another embodiment of the present disclosure. Surgical mesh 200 includes a body portion 210 including a plurality of fibers 220 extending therefrom. Fibers 220a, 220b, 220c, and 220d are disposed in predefined regions 212a, 212b, 212c, and 212d of body portion 210, both radially around and inward toward central portion 214. A clinician may chose to utilize all fibers 220 as illustrated in the present embodiment, or may utilize select fibers 220a, 220b, 220c, and 220d in each region 212a, 212b, 212c, and 212d of body portion 210 in order to customize and correctly align the mesh 200 with the tissue "T" (FIG. 4).

Surgical mesh 200 includes markings 240 disposed over at least a portion of the body portion 210. As illustrated, surgical mesh 200 includes markings 240 across the entire surface of the body portion 210. Markings 240 are illustrated as vertical and horizontal lines forming a grid to help, for example, delineate locations for folding the mesh 200 for insertion into tissue "T" (FIG. 4). It is envisioned that the mesh 200 may include any of a variety of markings, e.g., symbols, shapes, patterns, and/or colors, etc. to identify portions of the mesh 200 or to aid in positioning the body portion 210 against tissue.

Surgical meshes of the present disclosure may also include at least one bioactive agent. The term "bioactive agent", as used herein, is used in its broadest sense and includes any substance or mixture of substances that have clinical use. A bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. For example, a surgical mesh may be coated with an anti-adhesive to inhibit adhesion of the mesh to tissue and/or with a local anesthetic for temporary pain relief during implantation. It is envisioned that the bioactive agent may be applied to the surgical mesh in any suitable form of matter, e.g., films, powders, liquids, gels, combinations thereof, and the like.

Turning now to FIG. 4, an embodiment of using mesh 100 will be described. The use of surgical mesh 200 is substantially similar to that of surgical mesh 100 and, thus, will not be described herein for purposes of brevity. Initially, with reference to FIG. 4, surgical mesh 100 is positioned adjacent the tissue defect "D" of a patient to be repaired. Surgical mesh 100 is manipulated, e.g., by folding or rolling, such that mesh 100 is insertable through tissue defect "D" or through another tissue opening or incision (not shown) with minimal trauma. Once mesh 100 is positioned within the surgical site on a distal side of the tissue defect "D," mesh 100 re-opens and returns to its initial state.

In its initial state, mesh 100 extends completely across the tissue defect "D". Fibers 120 may be pulled proximally through tissue defect "D" to center the mesh 100 about tissue defect "D". In embodiments utilizing a guide 126, the fact that fibers 120 extend through guide 126 which is centrally disposed about mesh 100 automatically centers the mesh 100 relative to the tissue defect "D" upon grasping fibers 120 and pulling fibers 120 through tissue defect "D".

As can be appreciated, mesh 100 may be maneuvered into position against tissue by manipulating yarns 122a, 122b, 122c, and 122d individually or collectively. For example, to draw mesh 100 into approximation with tissue at the 12 o'clock position, the clinician would pull proximally on yarn 122a (which is engaged to body portion 110 at the 12 o'clock position). In order to inhibit lateral movement during approximation, if desired, the clinician would simply retain yarn 122c (which is disposed at the 6 o'clock position, opposite yarn 122a). Thus, the clinician can independently and incrementally pull and/or release each yarn 122a, 122b, 122c, and 122d to a desired position despite various anatomical considerations, e.g., varied tissue thicknesses, varied defect configurations, and/or various different tissue surface contours. In embodiments utilizing a main yarn 123, the tension provided on the main yarn 123 by the clinician will uniformly provide tension across the body portion 110 of the mesh 100.

Once properly positioned, the surgical mesh 100 may then be secured to tissue "T" via sutures (e.g., barbed sutures), staples, tacks, clips, or other fastening devices within the purview of those skilled in the art. After the mesh 100 is secured, the fibers 120 may be cut or simply left in place as described above.

Surgical meshes in according with the present disclosure may include a body portion configured to extend across a tissue defect and a plurality of fibers secured to the body portion. The plurality of fibers extends outwardly from the body portion and is gathered at a hub for handling by a clinician. In some embodiments, the plurality of fibers is coupled to the mesh via one of knitting, weaving, or interlacing each fiber through yarns forming the body portion. In other embodiments, the plurality of fibers is coupled to the mesh via one of knotting, tying, welding, adhering, and fusing each fiber to yarns forming the body portion.

In any of the presently disclosed embodiments, the body portion of the surgical mesh may include pre-defined regions each containing a portion of the plurality of fibers. The pre-defined regions may be symmetrically arranged about the body portion. The portion of fibers in each pre-defined region may be formed into a yarn. In embodiments in which the plurality of fibers is formed into yarns, each yarn may be color coded for visually identifying the pre-defined region of the body portion. The yarns may be commingled to form a main yarn. In embodiments, the yarns are commingled via one of weaving, knitting, braiding, interlacing, twisting, fusing, and aligning.

The surgical mesh of the present disclosure may be provided in a variety of shapes and sizes. Thus, in any of the above embodiments, the body portion of the surgical mesh may be circular. In such embodiments, the pre-defined regions of the body portion may correspond to the four quadrants of the circular body portion.

In any of the presently disclosed embodiments, the outer diameter of the body portion of the surgical mesh may include a stiffening ring.

In any of the presently disclosed embodiments, a central portion of the body portion of the surgical mesh may include a guide through which the plurality of fibers may extend outwardly.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the subject matter of the present disclosure is not to be limited by what has been particularly shown and described, and such modifications and variations are intended to come within the scope and spirit of the claims appended hereto.

What is claimed is:

1. A surgical mesh comprising:
a body portion configured to extend across a tissue defect, the body portion including pre-defined regions, each pre-defined region including a plurality of individual fibers, each individual fiber including a first portion secured to the body portion prior to forming a yarn and a second portion extending outwardly from a proximal surface of the body portion, wherein the second portions of the plurality of individual fibers of each pre-defined region are gathered to form at least one yarn thereby providing multiple yarns, the multiple yarns passing through a guide on a central portion of the body portion gathering at a common location for handling by a clinician.

2. The surgical mesh according to claim 1, wherein the first portions of the plurality of individual fibers are coupled to the mesh via one of knitting, weaving, or interlacing each fiber through the body portion.

3. The surgical mesh according to claim 1, wherein the first portions of the plurality of individual fibers are coupled to the mesh via one of knotting, tying, welding, adhering, and fusing each fiber to the body portion.

4. The surgical mesh according to claim 1, wherein the pre-defined regions are symmetrically arranged about the body portion.

5. The surgical mesh according to claim 1, wherein each yarn of the multiple yarns is color coded for visually identifying the pre-defined region of the body portion.

6. The surgical mesh according to claim 1, wherein the multiple yarns are commingled to form a main yarn.

7. The surgical mesh according to claim 6, wherein the multiple yarns are commingled via one of weaving, knitting, braiding, interlacing, twisting, fusing, and aligning.

8. The surgical mesh according to claim 1, wherein the body portion is circular.

9. The surgical mesh according to claim 8, wherein the pre-defined regions corresponding to quadrants of the circular body portion.

10. The surgical mesh according to claim 1, wherein an outer diameter of the body portion includes a stiffening ring.

11. The surgical mesh according to claim 1, wherein the plurality of individual fibers are fabricated from absorbable materials.

12. A method for repairing a tissue defect, comprising the steps of:

providing a mesh including a body portion including pre-defined regions, each pre-defined region including a plurality of individual fibers, each individual fiber including a first portion secured to the body portion prior to forming a yarn and a second portion extending outwardly from a proximal surface of the body portion, wherein the second portions of the plurality of individual fibers of each pre-defined region are gathered to form at least one yarn thereby providing multiple yarns, the multiple yarns passing through a guide on a central portion of the body portion gathering at a common location, inserting the mesh through a tissue defect such that the mesh extends across the tissue defect and at least one of the multiple yarns extends proximally through the tissue defect; and adjusting the tension on at least one of the multiple yarns extending through the tissue defect to position the mesh uniformly against tissue.

13. The method according to claim 12, wherein the step of adjusting the tension further includes manipulating a main yarn formed from a commingling of the multiple yarns.

14. The method according to claim 12, further comprising applying fasteners to the mesh to secure the mesh to tissue surrounding the tissue defect.

* * * * *